United States Patent
Minnigh et al.

(10) Patent No.: US 8,213,572 B2
(45) Date of Patent: Jul. 3, 2012

(54) RETROFITABLE LONG-LENGTH DIGITAL RADIOGRAPHY IMAGING APPARATUS AND METHOD

(76) Inventors: Todd R. Minnigh, Pittsford, NY (US); Xiaohui Wang, Pittsford, NY (US)

( * ) Notice: Subject to any disclaimer, the term of this patent is extended or adjusted under 35 U.S.C. 154(b) by 151 days.

(21) Appl. No.: 12/538,930

(22) Filed: Aug. 11, 2009

(65) Prior Publication Data
US 2011/0038454 A1   Feb. 17, 2011

(51) Int. Cl.
G01N 23/04 (2006.01)
G01N 23/083 (2006.01)
H05G 1/02 (2006.01)
H05G 1/10 (2006.01)
G21K 1/04 (2006.01)

(52) U.S. Cl. ......... 378/62; 378/95; 378/98.12; 378/145; 378/205

(58) Field of Classification Search ............. 378/51, 378/55, 62, 68, 91, 96, 98, 98.8, 98.12, 114, 378/145–147, 150, 189, 204–206, 210, 95
See application file for complete search history.

(56) References Cited

U.S. PATENT DOCUMENTS

| | | | |
|---|---|---|---|
| 4,454,606 A * | 6/1984 | Relihan | 378/97 |
| 4,613,983 A | 9/1986 | Yedid et al. | |
| 5,111,045 A | 5/1992 | Konno et al. | |
| 5,123,056 A | 6/1992 | Wilson | |
| 5,130,541 A | 7/1992 | Kawai | |
| 5,986,279 A | 11/1999 | Dewaele | |
| 6,333,962 B1 * | 12/2001 | Kitaguchi et al. | 378/57 |
| 6,454,460 B1 * | 9/2002 | Ramanathan et al. | 378/207 |
| 6,807,250 B2 | 10/2004 | Wang et al. | |
| 6,895,076 B2 | 5/2005 | Halsmer et al. | |
| 6,944,265 B2 | 9/2005 | Warp et al. | |
| 7,177,455 B2 | 2/2007 | Warp et al. | |
| 7,265,355 B2 | 9/2007 | Chang et al. | |
| 7,555,100 B2 | 6/2009 | Wang et al. | |
| 7,734,013 B2 * | 6/2010 | Kashiwagi et al. | 378/108 |
| 2005/0129298 A1 | 6/2005 | Warp et al. | |
| 2008/0152088 A1 | 6/2008 | Wang et al. | |

FOREIGN PATENT DOCUMENTS
EP   0 919856 A1   6/1999
* cited by examiner

*Primary Examiner* — Anastasia Midkiff

(57) ABSTRACT

An apparatus for obtaining a long-length x-ray image of a subject, has an x-ray source and a first sensor that generates a first signal that indicates termination of x-ray emission from the x-ray source. A digital radiography detector is energizable to generate image data after receiving x-ray emission from the x-ray source. A detector transport apparatus is actuable in accordance with the first signal to translate the digital radiography detector from at least a first detector position to a second detector position for generating image data at each detector position. A processor in communication with the digital radiography detector obtains the image data of the subject that is generated from the detector.

19 Claims, 13 Drawing Sheets

RETROFITABLE LONG-LENGTH DIGITAL RADIOGRAPHY IMAGING APPARATUS AND METHOD

FIELD OF THE INVENTION

This invention relates generally to digital radiographic imaging, and in particular to the acquisition of multiple, standard sized radiographic images for constructing a larger composite radiographic image.

BACKGROUND OF THE INVENTION

Full spine and full leg radiographic examinations, useful for assessment of scoliosis and for leg length, angulation, and deformity measurement and other diagnostic functions, require images that exceed the length of normal-sized radiographic films or other types of receiver media. In conventional practice, this extended- or long-length imaging (LLI) problem has been addressed using either of two basic approaches. The first approach uses an extra-long, non-standard sized imaging detector. This approach is straightforward and feasible when using x-ray film as the imaging medium, but becomes costly and impractical when using various types of digital radiography media. With Computed Radiography (CR) media, in which a photostimulable phosphor storage sheet or plate is exposed and digitally scanned in separate operations, the dimensions of the storage medium can be constrained by the dimensions of the CR cassette that houses the medium. There may be some flexibility for extending the size of the CR medium, as taught, for example, in U.S. Pat. No. 5,130,541 entitled "METHOD OF AND APPARATUS FOR RECORDING AND READING RADIATION IMAGE" to Kawai that shows the use of an elongated CR plate for long-length imaging. However, this approach may prove impractical and expensive, difficult to justify for most radiography installations.

For Digital Radiography (DR) detectors that directly transform received exposure energy to digital image data, the problem of extended-length imaging is much more complex and the fabrication and use of an oversized DR detector is seen as prohibitively costly and impractical. Instead, a second approach for extended-length imaging obtains portions of the full image on two or more standard-size detectors, adjusting the translational or angular position of the x-ray source between each image, then uses digital image processing to stitch the obtained sub-images together. This approach is taught, for example, in U.S. Pat. No. 5,111,045, entitled "APPARATUS FOR RECORDING AND READING RADIATION IMAGE INFORMATION" to Konno et al.; in U.S. Pat. No. 5,986,279, entitled "METHOD OF RECORDING AND READING A RADIATION IMAGE OF AN ELONGATE BODY" to Dewaele; and EP 0 919856A1, entitled "METHOD AND ASSEMBLY FOR RECORDING A RADIATION IMAGE OF AN ELONGATE BODY" to Dewaele et al. A variation on this approach also sequentially re-positions a single DR detector along the anatomy to be imaged so that the same detector is used to obtain images at two or more positions.

Among the factors that make long-length imaging using a single DR detector more complex is the image transfer and refresh timing of the DR detector hardware. Even with higher speed circuitry and advanced techniques for image storage and transfer, the time interval required between image captures can be on the order of a few seconds. Inadvertent movement of the patient between images can present difficulties for reconstruction of the full length image from individual component images. The timing of DR exposure and detector and radiation source movement or adjustment between images provides significant complications for the designer of DR systems.

Solutions that have been proposed thus far generally require complex interaction and coordination between components that are shifted between positions for obtaining individual images. Translation of the imaging detector relative to the patient has been proposed using various techniques. For example, U.S. Pat. Nos. 4,613,983 entitled "METHOD FOR PROCESSING X-RAY IMAGES" to Yedid et al. and 5,123,056 entitled "WHOLE-LEG X-RAY IMAGE PROCESSING AND DISPLAY TECHNIQUES" to Wilson disclose X-ray systems for imaging a human subject lying on a table. Either the table or both the X-ray source and table are then moved to produce, in quick succession, a series of overlapping electronic images which are then combined into an elongated image for display or printing. Similarly, Warp et al. in U.S. Pat. No. 7,177,455 entitled "IMAGE PASTING SYSTEM USING A DIGITAL DETECTOR" describes shifting the position of a DR detector and adjusting the corresponding position of the x-ray source for obtaining individual images that can be stitched together using digital techniques.

Commonly assigned U.S. Pat. No. 6,807,250 entitled "COLLIMATION DEVICE AND METHOD FOR ACQUIRING A RADIATION IMAGE OF A LONG BODY PART USING DIRECT DIGITAL X-RAY DETECTORS" to Wang et al. describes the use of a shutter or other opaque element having an opening that is used in conjunction with the x-ray detector and that can be variably positioned relative to a movable DR detector in order to obtain each separate image for a long-length imaging exam. However, while this solution addresses the need for adjustment of the x-ray source, a mechanism is employed for synchronizing the position of the shutter relative to the detector, which typically requires a controller that also tracks DR detector position.

Although techniques disclosed thus far may be workable for obtaining separate images of the patient that can then be stitched together, a number of practical problems remain. In particular, the proposed solutions noted earlier each require relatively complex and costly systems. For example, multiple control processors are typically used to provide and to coordinate relative movement between the patient, exposure device, and detector. Because of this, these solutions would not be readily adaptable for use as retrofit apparatus for existing x-ray systems, but would need installation of new exposure, sensing, and control and monitoring equipment.

Thus, it can be appreciated that there is a need for a long-length imaging solution that is relatively low cost and that allows x-ray exposure energy to be directed to a digital radiography detector that may be variably positioned at any of a sequence of positions along a linear path in order to obtain a portion of the longer image at each position. A solution that meets these requirements without requiring complex communication between detector-positioning and beam-positioning subsystems would be particularly advantageous.

SUMMARY OF THE INVENTION

It is an object of the present invention to advance the art of diagnostic imaging, particularly for long-length x-ray imaging. With this object in mind, the present invention provides an apparatus for obtaining a long-length x-ray image of a subject, comprising: an x-ray source; a first sensor that generates a first signal that indicates termination of x-ray emission from the x-ray source; a digital radiography detector that is energizable to generate image data after receiving x-ray emission from the x-ray source; a detector transport apparatus actuable in accordance with the first signal to translate the digital radiography detector from at least a first detector position to a second detector position for generating image data at each detector position; and a processor in communication with the digital radiography detector for obtaining the image data of the subject that is generated from the detector.

It is an advantage of the present invention that it provides a retrofit solution for long-length imaging for an x-ray system.

These objects are given only by way of illustrative example, and such objects may be exemplary of one or more embodiments of the invention.

Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
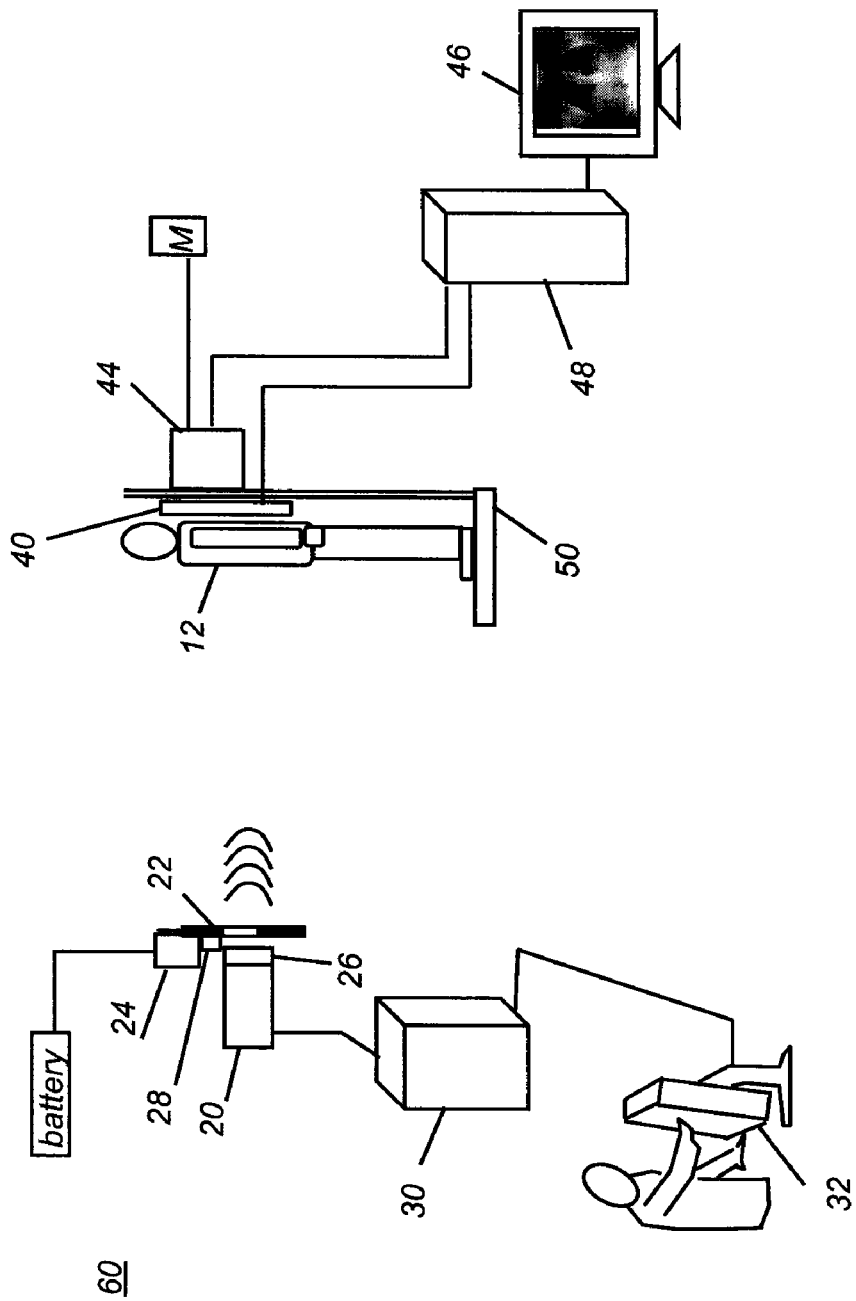
FIG. 1 shows a schematic diagram of an imaging apparatus for providing long-length DR imaging of a patient.

The following is a detailed description of the preferred embodiments of the invention, reference being made to the drawings in which the same reference numerals are used to identify the same elements of structure in each of the several figures.

Reference is made to commonly assigned U.S. Pat. No. 7,555,100 entitled LONG LENGTH IMAGING USING DIGITAL RADIOGRAPHY (Wang et al.).

Unlike conventional system-based approaches for long-length imaging that track position and synchronize relative movement of both the DR detector and the radiation source, embodiments of the present invention provide an "asynchronous" solution that triggers movement of both the radiation source and the DR detector according to the exposure timing itself. That is, the apparatus and methods of the present invention detect when exposure begins and terminates and use the fact that exposure has just been completed to initiate movement of both the directed beam of x-rays and the DR detector. By directly sensing exposure termination, the solution of the present invention can be dissociated from system-wide control logic, allowing this solution to provide a readily usable retrofit for existing imaging systems, without the need to modify or replace existing equipment and minimizing or eliminating requirements for site re-certification or other regulatory complications.

In the context of the present disclosure, the individual images that are combined to form a full-length or "composite" image are termed "component images". One consideration for effective long-length imaging relates to the gap at the interface between adjacent images. Accurate stitching of adjacent images, as noted in the background section given earlier, requires some overlap between their respective boundaries.

Referring to FIG. 1, there is shown a schematic diagram of an imaging apparatus 60 for providing long-length DR imaging of a patient 12 or other subject according to an embodiment of the present invention. An x-ray tube 20 serves as the x-ray source that provides the needed exposure radiation for imaging, under the control of control circuitry 30 that has an operator console 32 for entry of setup and operation commands. X-ray tube 20 has a collimator 26 and an additional exposure mask 22 that controls the distribution of radiation that is provided. A mask translation control 24 cooperates with a signal from a sensor 28 to shift the position of exposure mask 22 once an exposure is obtained, that is, following exposure termination. Exposure termination can be indicated directly, such as using a signal transition, or by using the signal transition along with a timer that provides an indicator based on the timed interval.

In FIG. 1, imaging apparatus 60 uses a single DR detector 40 that mounts on a transport column 50 or other transport mechanism for providing movement along the length direction, corresponding to the patient's height in this example. DR detector 40 is energizable to generate image data after receiving x-ray emission from the x-ray source. A DR translation control 44 provides the needed sensing and control circuitry and is actuable for translating the position of DR detector 40 to the next position between exposures, according to the signal indicating that exposure has been obtained and has terminated. Various embodiments for DR translation control 44 use one or more springs, servo motors, solenoids with a gravity-feed mechanism, and other devices, as well as combinations using two or more devices (shown as mechanism M in FIG. 1). A DR control processor 48 obtains the digital data from DR detector 40 and also provides control signals for DR translation control 44. A display 46 in communication with DR control processor 48 then displays each obtained image.

Still referring to FIG. 1, the utility of imaging apparatus 60 as a retrofit within an existing DR imaging site can be appreciated. For providing the directed radiation signal, exposure mask 22 and its associated sensor 28 and mask translation control 44 can be added onto the existing collimator 26 without any needed rewiring or rework of system components. Moreover, no communication link or processing signal transfer is required between mask translation control 24 and DR control processor 48 for synchronizing the re-positioning or translation of both exposure mask 22 and DR detector 40. Instead, the sensing and control components that initiate and effect the necessary movement of both exposure mask 22 and DR detector 40 are separate from each other and can be considered to operate asynchronously. This allows ready use of components of the present invention for retrofit of an existing imaging system and also allows a fully integrated system solution to the long-length imaging problem.

Figure 2:
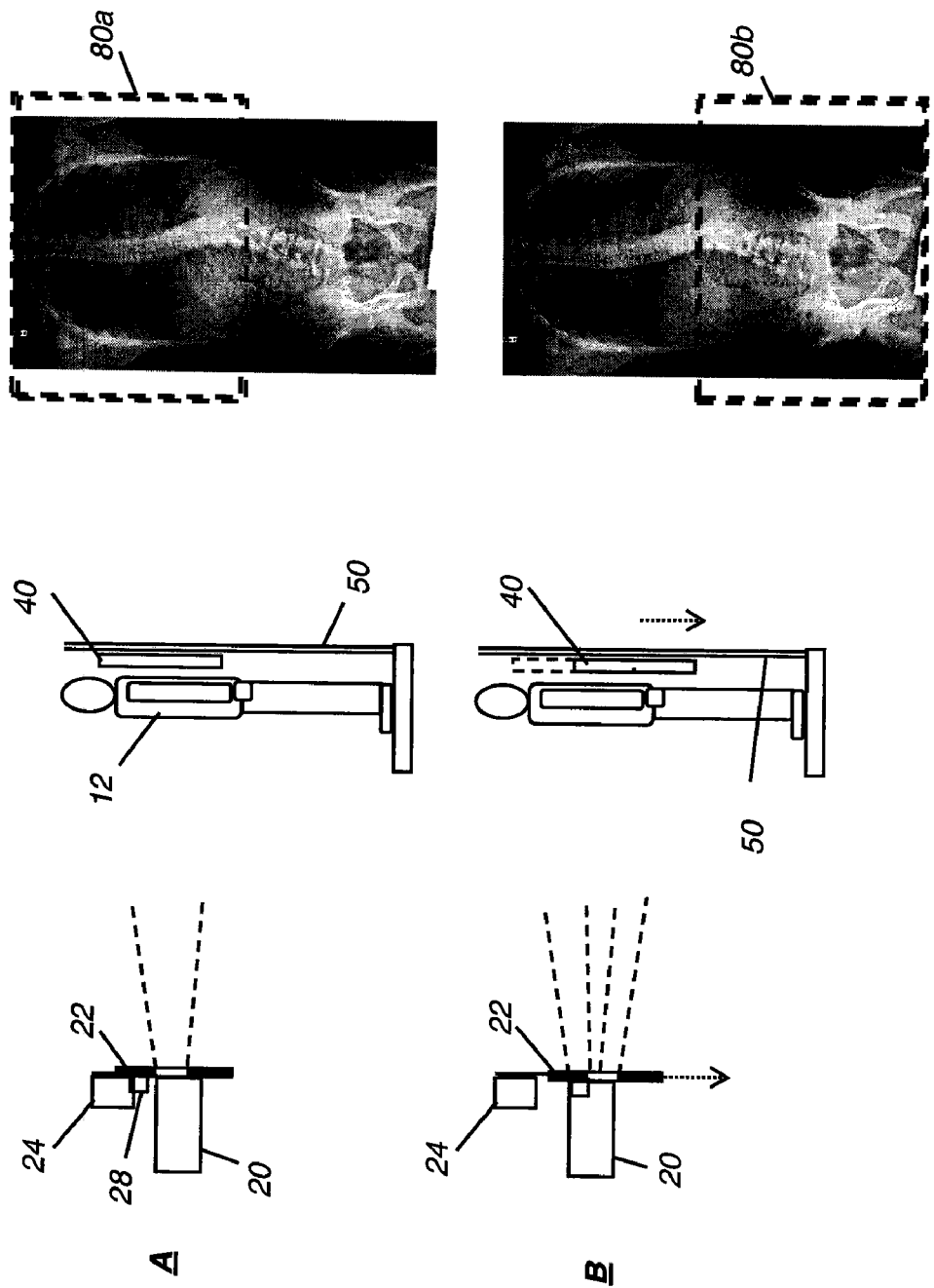
FIG. 2 shows a schematic diagram with images obtained at two positions.

The diagram of FIG. 2 shows the basic translation that is required for both exposure mask 22 and DR detector 40 in an example in which two component images are obtained for stitching together to obtain a composite long-length image. Representative images are shown at the right in this figure. At position A, exposure mask 22 directs the radiation to DR detector 40 at an upper position, such as for chest imaging. An upper position image 80a is obtained. Then, once upper position image 80a is obtained, exposure mask 22 is then translated to the B position to obtain lower position image 80b. The height and angle of X-ray tube 20 can be the same as at A; on the signal side, only exposure mask 22 is moved at B.

Figure 3:
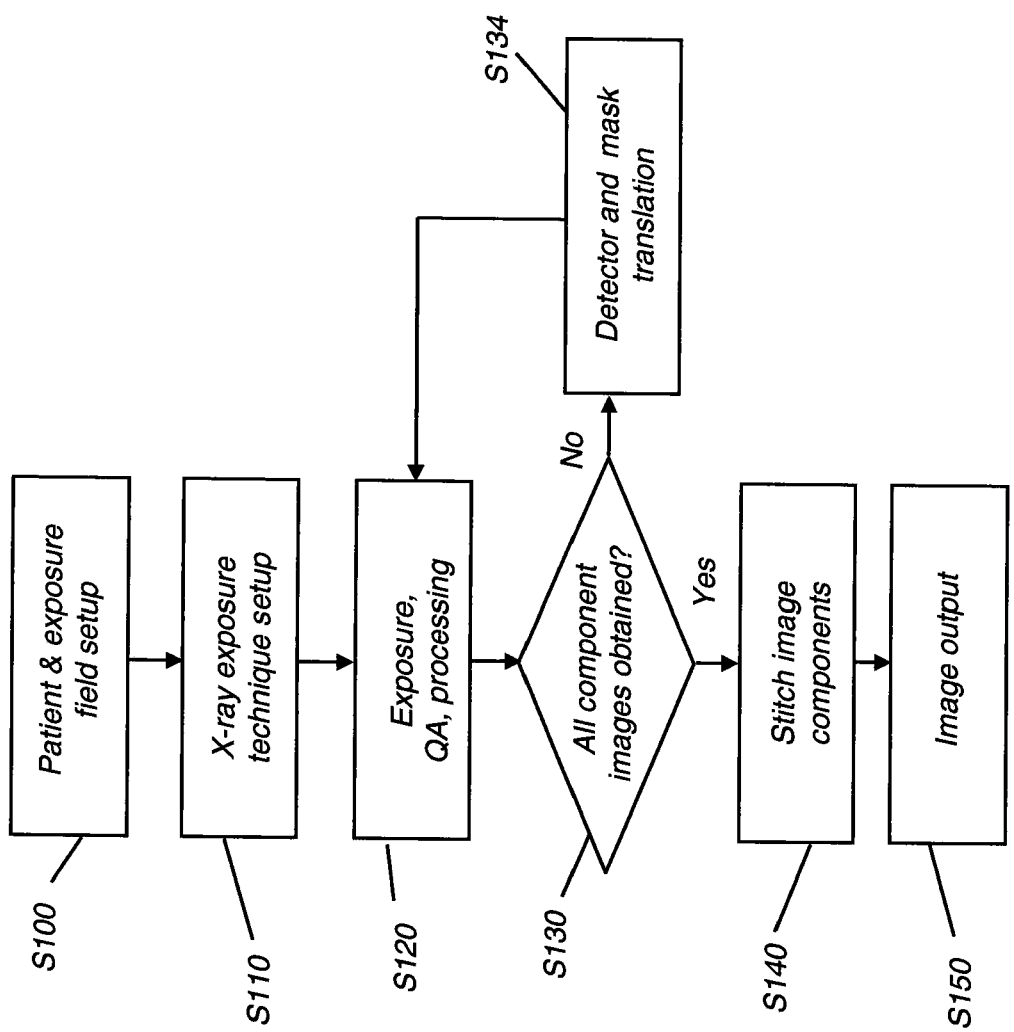
FIG. 3 is a logic flow diagram showing a sequence for obtaining a long-length image using the apparatus of the present invention.

The logic flow diagram of FIG. 3 shows steps for long-length imaging using the apparatus and method disclosed herein. In a setup step S100, the radiology technologist positions the patient as needed for the requirements of the exam. This may mean positioning in the upright or supine position, for example. Then, using system controls or manual positioning, or some combination of the two, the technologist sets up the exposure field for long-length imaging. In one embodiment, the technologist simply sets an initial imaging position and then sets up one or more additional imaging positions, according to factors such as the length of the area being imaged, the amount of overlap that is used between images, the positions of overlap areas relative to patient anatomy, the dimensions of the DR detector itself, and other factors. This setup thus determines the number of images that must be obtained and their relative positions. Additional details on setup factors and considerations for long-length imaging are given subsequently.

The technologist has a number of tools available from imaging apparatus 60 for facilitating long-length imaging setup. For example, for setting up the initial positions of x-ray tube 20 and the initial height of DR detector 40, the technologist typically uses the visible light aiming tool that is available with the x-ray tube collimator aperture, thereby identifying the desired anatomical region of the patient. The visible light from the collimator, representative of the full, actual x-ray exposure coverage, assists in determining the total exposure area on the patient in similar manner to that used for a screen film system. The system for one embodiment uses the area marked by visible light as the system-controlled exposure area as well.

Note that, in setup step S100, the collimator size may exceed the dimensions of the full sized exposure field defined by the DR detector 40 dimensions. Positional and component distance feedback, including information about collimator size, can be provided to operator console 32 control logic for the imaging system (FIG. 1). This allows computation of the number of exposures needed in an exposure series and computation of the actual exposure size, as is described subsequently. In this way, a long-length imaging mode of system operation is obtained using setup step S100. Additional manual procedures may also be required, such as manually setting one or more mask 22 or DR detector 40 locations, for example.

Continuing with the sequence of FIG. 3, an x-ray exposure technique setup step S110 follows, in which the technologist determines and sets up the overall x-ray technique parameters that provide instructions for imaging, as described in more detail subsequently. Then, to begin an exposure and processing step S120, the technologist initiates the full exposure series by a command entry, such by pressing an exposure button on operator control console 32, for example. A signal then indicates termination of exposure. After the exposure image is captured, a decision step S130 then determines whether or not one or more additional component exposures are still needed to complete the series. If so, a translation step S134 is then executed, in which both DR detector 40 and collimator mask 22 are translated to the next imaging position, in preparation for another iteration of step S120. If all images have been captured, an image stitching step S140 is executed and an image output step S150 provides the final composite long-length image.

It should be noted that the basic sequence shown in FIG. 3 allows a number of variations in different embodiments of the present invention. For example, Quality Assurance (QA) information may be generated and assessed at any of a number of different points as images are captured. In one embodiment, the basic sequence of FIG. 3 operates in a fully automated mode, for which a single command entry or button press initiates the full sequence for obtaining and stitching together two or more images. An interrupt is provided to give the operator the capability to stop this continuous sequence. In a prompting mode, the technologist may be prompted for obtaining each component image following translation step S134, for example. Using this sequence, the technologist manually initiates each of the individual exposures in a series of exposures, such as by pressing a button on operator console 32, for example. Either mode would thus allow the technologist to stop the imaging process for any reason, such as due to patient condition, excessive movement, safety, or other concern.

To facilitate image stitching, in one embodiment, encoders or other suitable types of sensors are used to control and detect position and operation of various mechanical components of the system and their operating parameters, including, but not limited to, the detector position, tube position, mask position, tube rotation angle, collimator aperture size, and collimator shutter position.

Setup Step S100 Parameters

Figure 4:
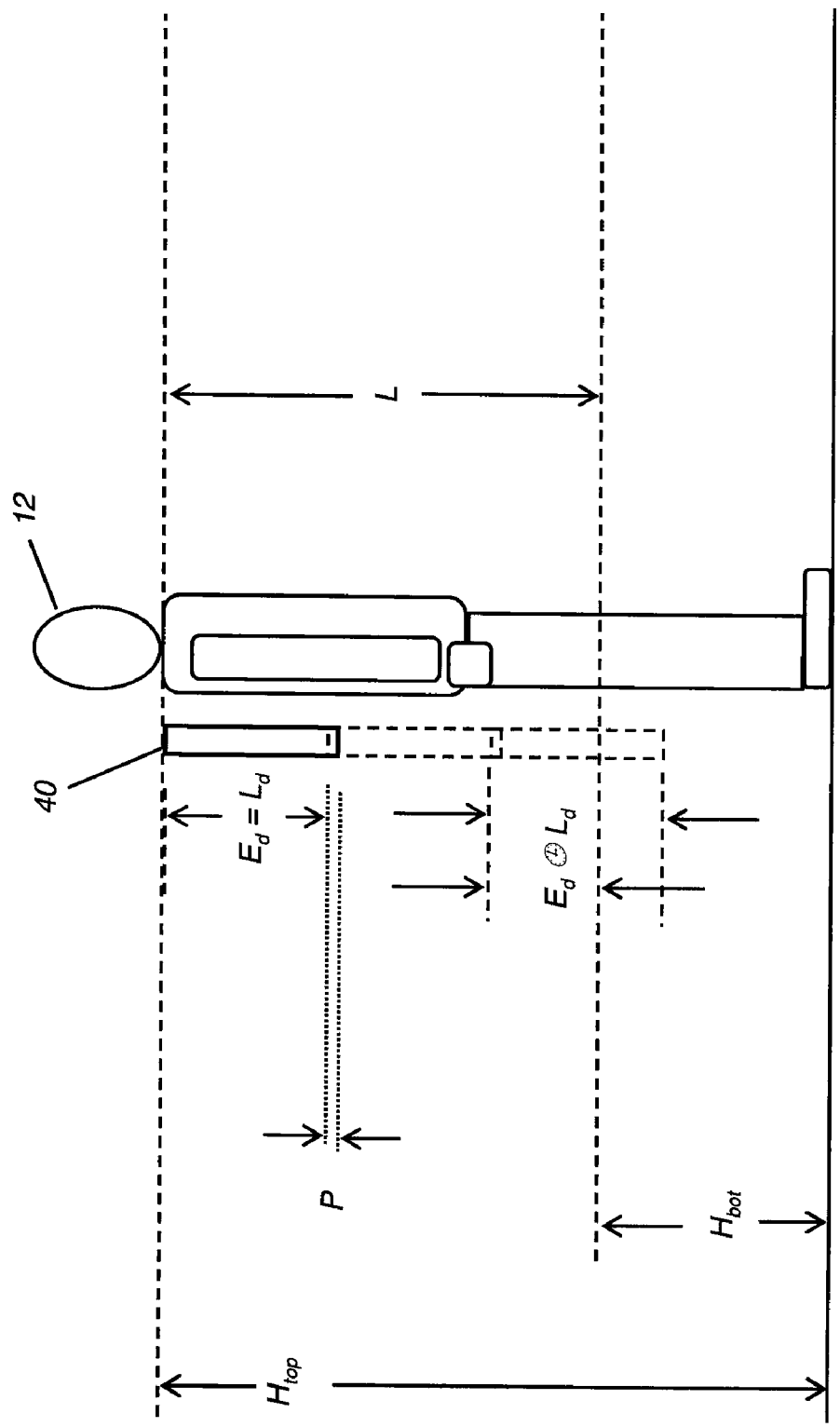
FIG. 4 is a schematic diagram showing detector positioning for multiple images.
Figure 5:
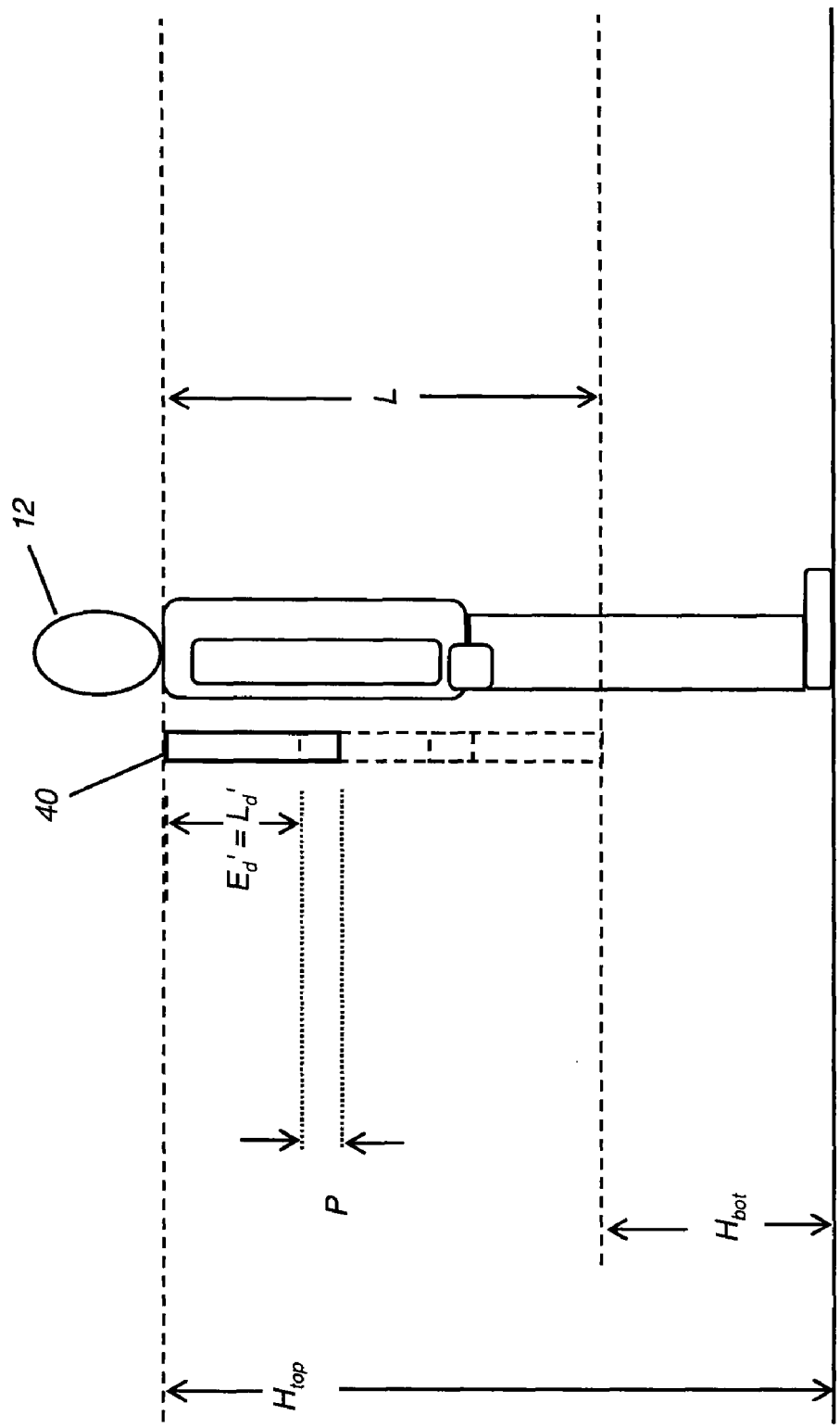
FIG. 5 is a schematic diagram showing detector positioning for multiple images with images of the same dimension.

Setup step S100 determines the number of component images n that must be obtained for a particular patient and identifies the required positions of DR detector 40 and collimator mask 22 for providing each of these images. FIGS. 4 and 5 show examples in which three images are obtained for stitching together in one embodiment. For these examples, a number of variables are defined, as follows:

L is the overall exposure length that is needed;

$L_d$ or $L_d'$ gives the effective exposure length on the DR detector, available for each single image;

$E_d$ or $E_d'$ gives the exposure field size, as computed, usually set equal to the corresponding effective exposure length $L_d$ or $L_d'$;

P is the minimum exposure overlap that is required between images for stitching.

In the example shown in FIG. 4, the number of exposures N is computed, such as using the following:

$$N=(\text{int})[(L-P)/(L_d-P)+1]$$

wherein the (int) operator takes the integer part of the result given in brackets [ ].

In step S100 (FIG. 3), the x-ray technologist initially establishes the height of the image area, thus the exposure length L, by specifying at least two variables:

$H_{top}$: Floor to top of radiation field;

$H_{bot}$: Floor to bottom of radiation field.

Figure 6A:
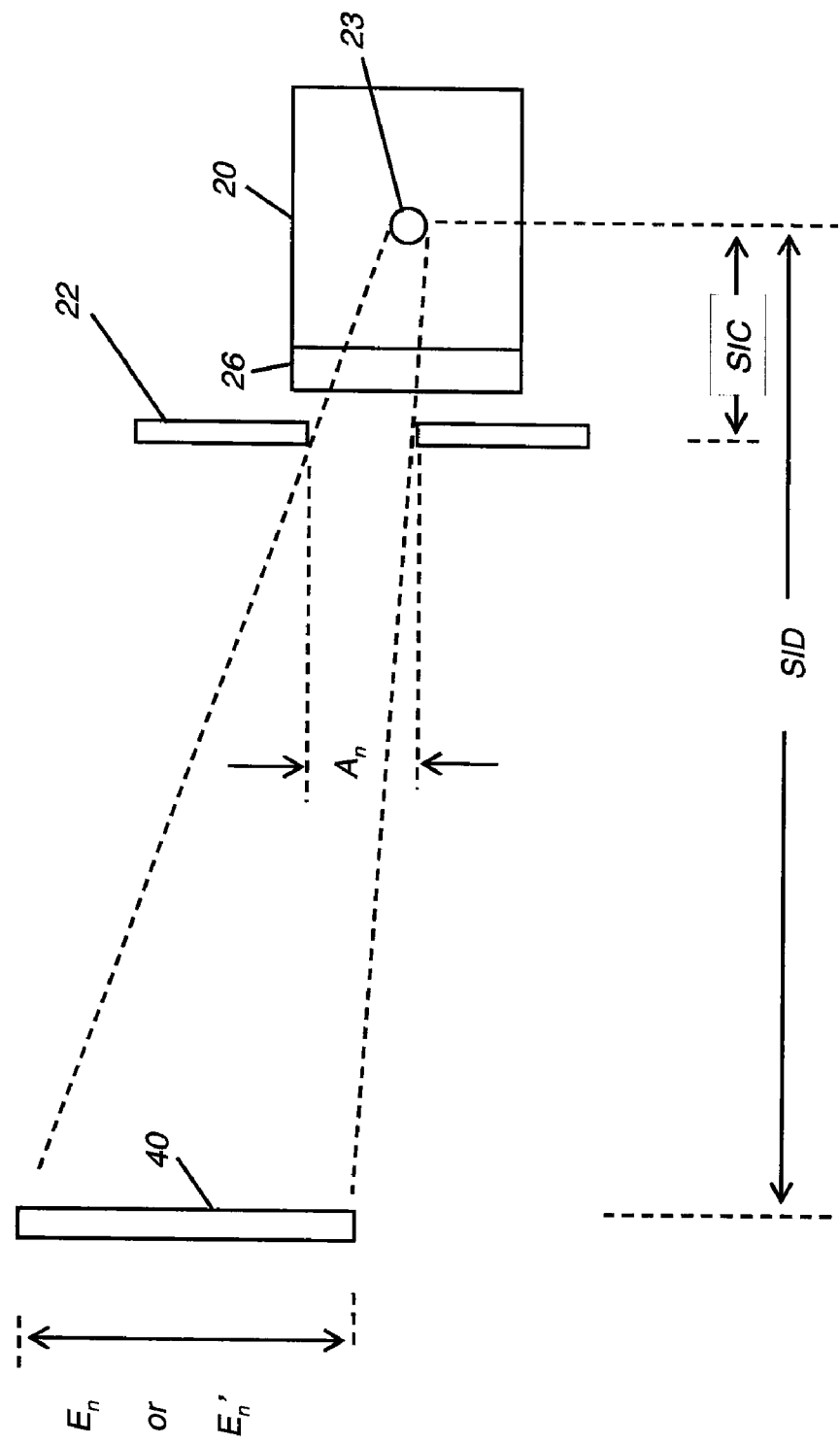
FIGS. 6A and 6B are schematic diagrams showing the geometry of the x-ray source relative to the detector at different positions.
Figure 6B:
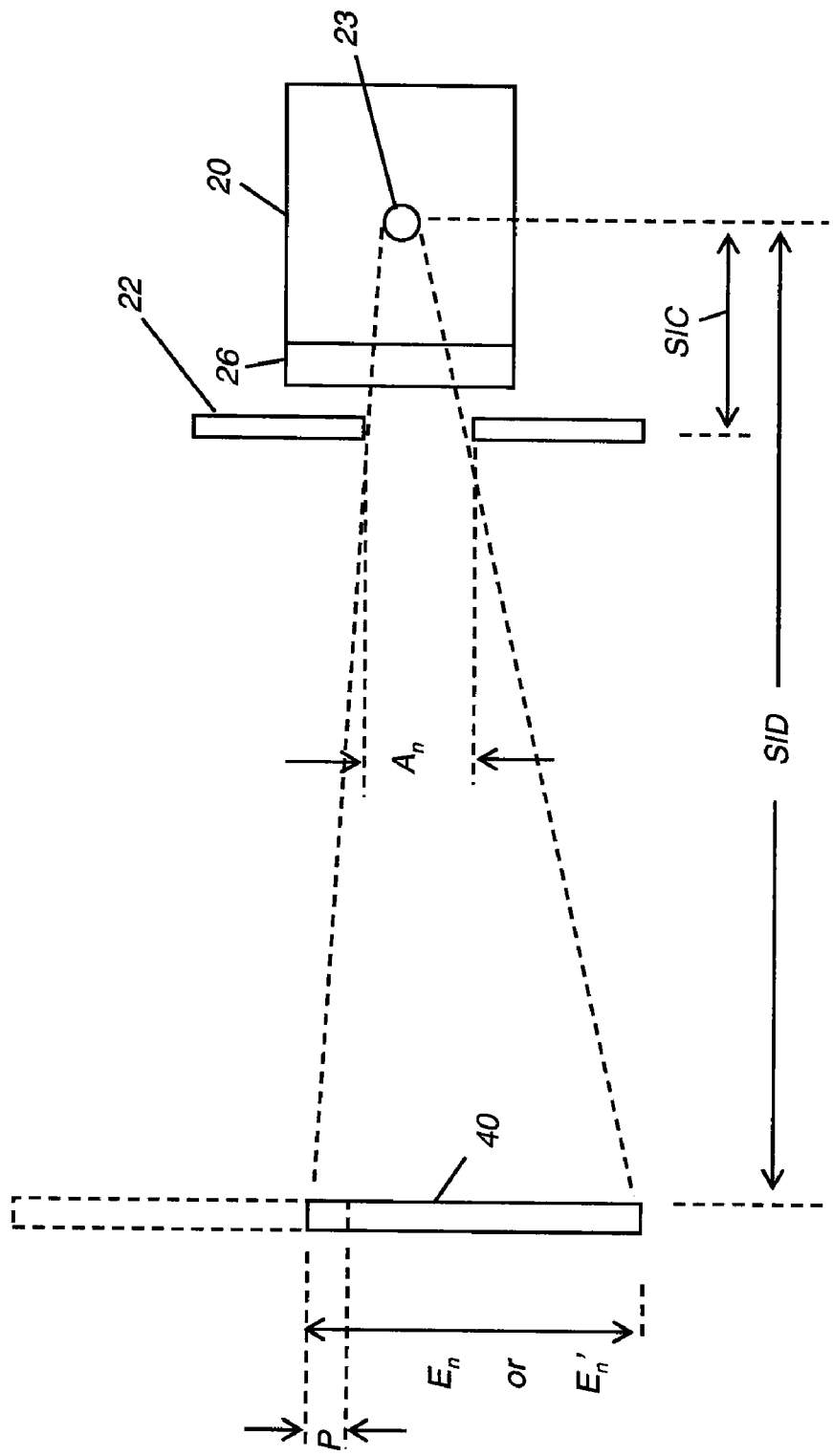

FIGS. 6A and 6B show how the appropriate aperture size $A_n$ of mask 22 corresponds to the size of the effective radiation field, $E_n$ or $E_n'$, and how this field is manipulated by modifying the collimator 26 aperture with exposure mask 22 that is disposed adjacent x-ray tube 20. As is shown in FIGS. 6A and 6B, x-ray tube 20 provides a point source at x-ray focal spot 23. Assuming that collimator 26 has a symmetric aperture around the central x-ray beam (which is common in conventional collimator design), an appropriate exposure mask 22 size can be calculated based on the effective exposure field and the magnification factor:

$$A_n = E_n \times SIC/SID \text{ or}$$

$$A_{n'} = E_{n'} \times SIC/SID$$

wherein SIC is the distance between x-ray focal spot 23 and exposure mask 22, and SID is the distance between x-ray focal spot 23 and detector 40.

In some embodiments where mask 22 is used, x-ray tube 20 remains stationary between exposures. Its radiation field is then set up initially to extend over the full image height. In practice, this can be accomplished by adjusting the collimator so that the visible collimator light illuminates the full field desired for imaging, without consideration of detector 40 height. Sensors on collimator 26 itself enable reporting the size of the collimator opening to system logic, or this dimension can be measured in some other way. This data is then usable in combination with other information on source-to-detector distance (SID) in order to determine the full extent of the image area, with length corresponding to exposure length L as shown in FIGS. 4 and 5.

Knowing length L, overlap P, and effective exposure length parameter $L_d$, the number of component exposures that are needed can be readily computed. For the embodiment of FIG. 4, three exposures are needed. One exposure in the series that is obtained uses only a smaller portion of detector 40. Alternately, in the embodiment shown in FIG. 5, substantially equal portions of detector 40 of dimension $E_d' = L_d'$ are used for each of the three exposures, with the overlap value P changed from the FIG. 4 case accordingly. Parameter $H_{top}$, or alternately $H_{bot}$, along with length L, serves to locate the starting-point or ending point of a series of overlapped images for long-length imaging.

The calculations that are needed for positioning detector 40 and mask 22 for long-length imaging are not complex and are well within the scope of capabilities of an experienced radiology technologist. The following general observations are particularly pertinent to the long-length imaging environment of embodiments of the present invention:

(i) The series of two of more images that are obtained may be taken in any order. In general, top-to-bottom, bottom-to-top, left-to-right, and similar sequencing based on adjacent position is more practical; however, there can be situations in which it is advantageous to change the positional ordering.

(ii) One or both collimator 26 and mask 22 settings are optionally adjustable to accommodate for images that have an exposure field that is smaller than $L_d$, as in the example of FIG. 5.

(iii) Mask aperture $A_n$ may or may not be adjustable between exposures, depending upon the equipment configuration.

(iv) In general, it is advantageous to use a sequence that minimizes the time between exposures. This reduces the likelihood of patient movement that can complicate registration and image stitching in step S140 (FIG. 3).

For the FIG. 4 example, where N exposures are taken in sequence from top to bottom, the effective exposure field size $E_n$ on the detector is the same, $L_d$, for the first N–1 exposures, but is smaller for the last exposure, $E_N$:

$$E_n = L_d \text{ when } n=1, 2, \ldots N-1 \text{ and}$$

$$E_N = L - [(N-1)L_d - (N-2)P]$$

With this arrangement, the vertical travel distance for detector 40 is the same to reach each exposure position. However, this requires a corresponding adjustment of the mask 22 aperture for the smaller exposure $E_N$. This may be impractical, as noted earlier.

The FIG. 5 embodiment is an alternate arrangement in which all of the exposure field sizes are equal, the vertical travel distance for detector 40 is the same to reach each exposure position, and the mask 22 aperture setting is the same for each exposure position. For FIG. 5, the following are computed as was described with reference to the example of FIG. 4:

a number of exposures required n;
a top $H_{top}$ and a bottom $H_{bot}$ of the radiation field;
an overall exposure length L; and
a minimum exposure overlap P required for stitching.

The exposure radiation fields $E_n$ are of equal size, and are obtained by setting an effective exposure field size $L_d'$ to:

$$L_d' = (L-P)/N + P.$$

In this method, an effective radiation field $E_n'$ (n=1, 2 ... N) will be the same, for all the exposures.

$$E_n' = L_d'$$

The calculation of tube/detector stop positions $H_n$ (for n=1, 2, ..., N) is obtained using:

$$H_n = H_{bot} + L_d'/2 + n \times (L_d' - P).$$

It can be appreciated that there are a number of ways by which exposure length and radiation field sizes and position can be calculated and that the above examples are illustrative of one approach. Other approaches are possible, including techniques that may change the size of exposure overlap P or other variable, for example.

Various levels of automation or technologist interaction are usable for setting up the sequence of exposures. In one embodiment, manual setup is used for detector 40 and mask 22 aperture positioning for multiple exposures. Prior to imaging, the technologist interacts with controller hardware to set up and store the needed detector 40 and mask 22 positions in memory, using the visible light aiming tool that is available with the x-ray tube collimator, for example, to manually set up each position. A logic command entered by the technologist then instructs the respective controller circuitry (FIG. 1) to remember each position.

Figure 7:
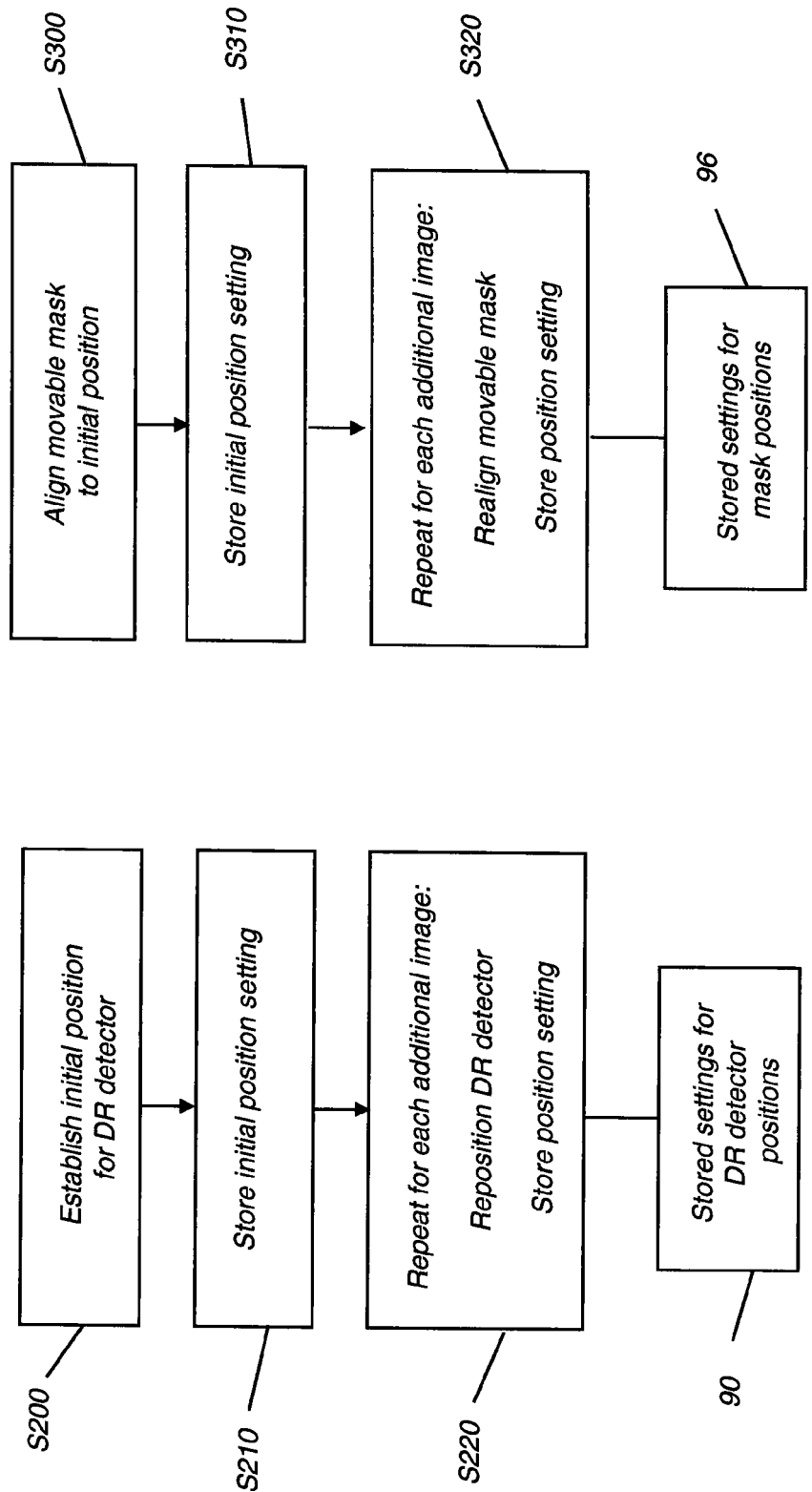
FIG. 7 is a logic flow diagram showing setup steps for storing position data for the mask and the detector in one embodiment.

In spite of the fact that both detector 40 and mask 22 move from one imaging position to the next following exposure, their respective translation control apparatus, DR translation control 44 and mask translation control 24, are set up and operate in an asynchronous manner, without requiring communication between them. The logic flow diagram of FIG. 7 shows the setup steps for obtaining the respective positions of DR detector 40 and movable mask 22 in one embodiment using manual positioning by the technologist. For this embodiment, an interactive session is used to store position data so that it is accessible to DR translation control 44. Interaction with the technologist is performed using command entries at DR translation control 44 or using the operator interface to DR control processor 48, for example.

For DR detector 40 positioning, shown in the left column of steps in FIG. 7, an initial setup step S200 obtains the first position for the detector. In a storage step S210, this initial position information is stored in a memory that is accessible to DR translation control 44. A looping step S220 then has the technologist repeatedly repositioning the DR detector and storing the settings for each of the subsequent DR detector positions. At the end of this process, stored settings 90 are then available for moving DR detector 40 to each position.

Mask 22 positioning, shown in the right column of steps in FIG. 7, is executed in similar fashion, coordinated by the technologist with the steps for DR detector positioning just described. An initial setup step S300 obtains the first position for mask 22. In a storage step S310, this initial position information is stored in a memory that is accessible to mask translation control 24. A looping step S320 then has the technologist repeatedly repositioning the mask and storing the settings for each of the subsequent mask positions. At then end of this process, stored settings 96 are then available for moving mask 22 to each position.

Using a sequence similar to that shown in the embodiment of FIG. 7, separate data for positioning the detector and the mask are obtained and stored in separate systems; hence, the asynchronous nature of this positioning arrangement. The technologist who performs this setup provides the needed "synchronization" upon setup by storing the appropriate position values for each exposure in the series.

In an alternate embodiment, the technologist may simply provide starting and ending coordinates for long-length imaging to the control logic that positions detector 40 and mask 22. Automated tools are then used for automatically obtaining suitable positions for DR detector 40 and movable mask 22 along the long-length imaging path, including calculating overlap P, amount of translation between exposures, and related values, as described earlier with reference to FIGS. 4, 5, 6A, and 6B. Stored algorithms then compute appropriate positions and sequencing for detector 40 and mask 22 positions. Other arrangements using varying amounts of technologist interaction and automated control and logic may be provided. It should be noted that even where automated tools are used, technologist review of machine-generated placement coordinate information and other factors is generally recommended.

Exposure Technique Setup Step S110

At the completion of setup step S100 (FIG. 3), the variable dimensional factors have been determined and any other mechanical setup needed for long-length imaging execution have been carried out. In the subsequent exposure technique setup step S110, a number of technique variables are determined by the technologist, including but not limited to kVp, mAs, automatic exposure control (AEC) usage, exposure compensation factor (ECF), beam filtration, and anti-scatter grid settings, for example. In film screen radiography for full-spine and full-leg exams, a specially built beam intensity compensation filter is commonly used to pre-attenuate the beam intensity such that the exposure on the film is more uniform across the whole patient anatomy for optimal film brightness and contrast, and to reduce unnecessary x-ray radiation to thinner parts of the patient anatomy. With the system as disclosed herein, since only a portion of the patient anatomy is imaged at any one time, the compensation filter is typically not employed. Rather, the system can use the AEC (Automatic Exposure Control) to automatically adjust the x-ray output during long-length imaging. In one embodiment, the AEC is used when acquiring each image of the exposure series.

Figure 8B:
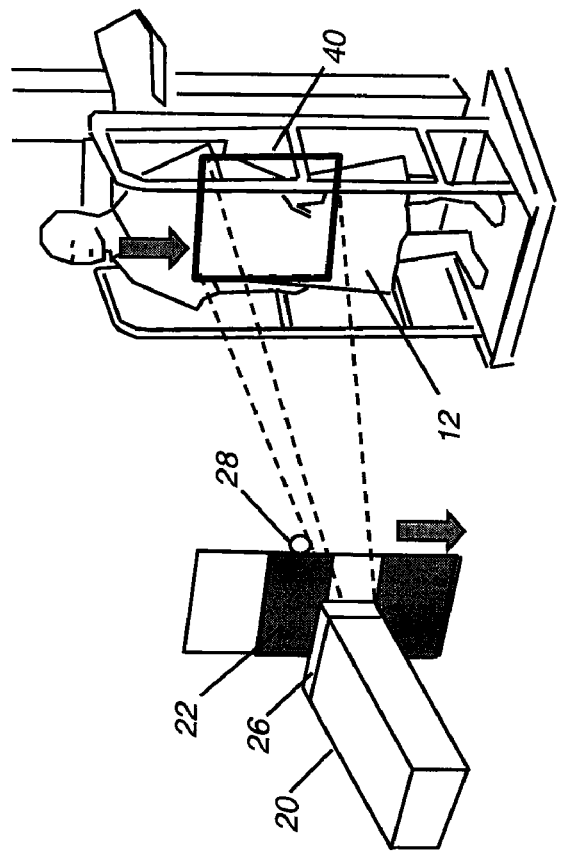
FIGS. 8A and 8B show how images are obtained in two positions using an embodiment of the present invention.
Figure 8A:
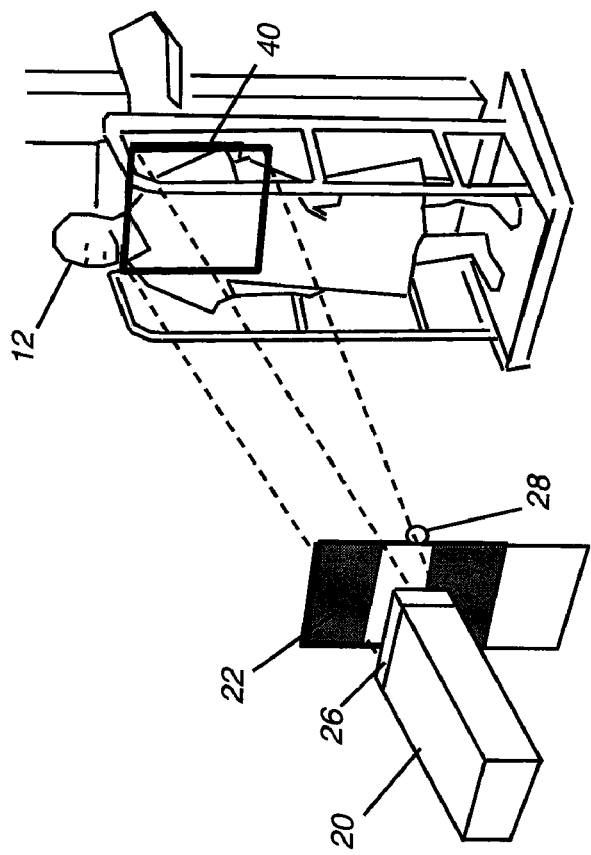
Figure 9:
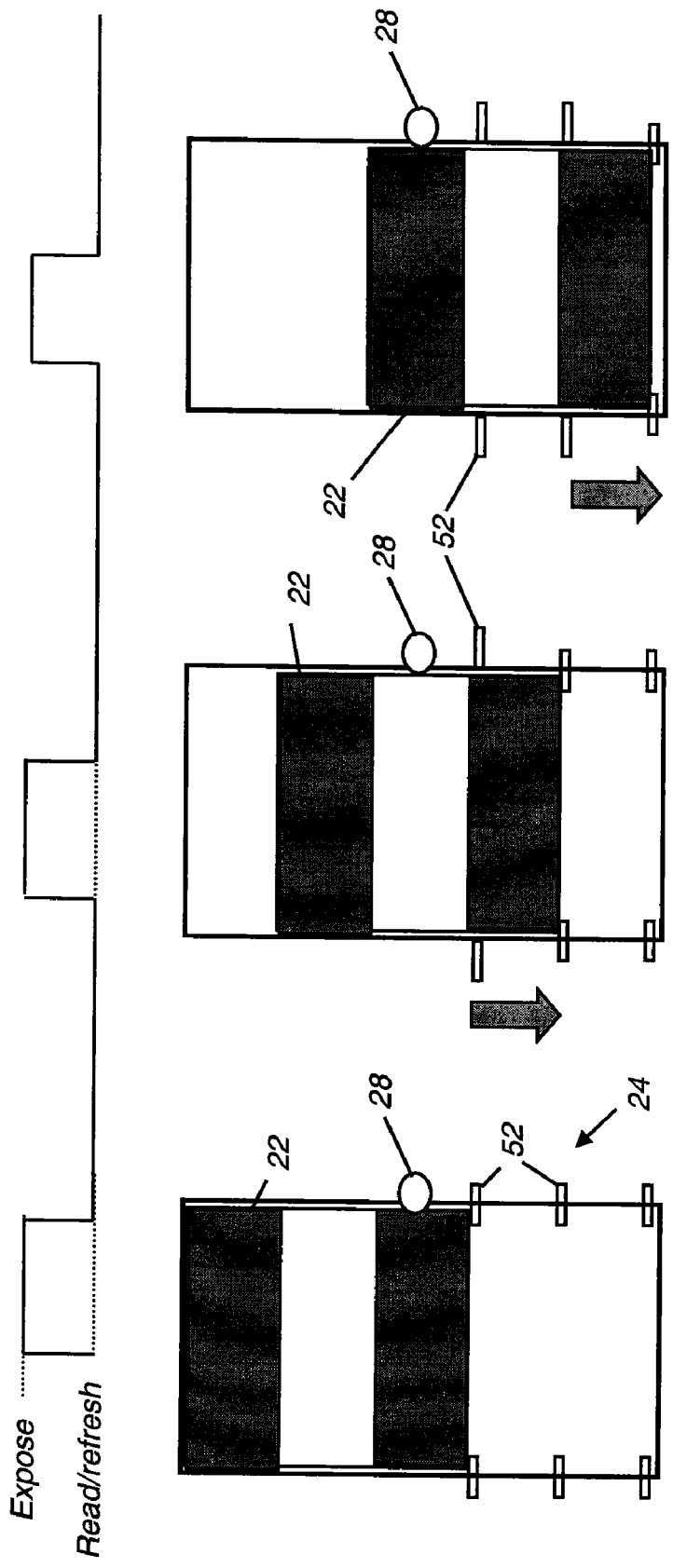
FIG. 9 is a schematic diagram showing positioning of an exposure mask relative to exposure and refresh timing.

For retrofit situations, the separate transport apparatus of the present invention, shown as mask translation control 24 and DR translation control 44, do not provide each other with a direct coordinating control signal, but use sensing methods to detect exposure and to trigger translation between positions, or to indicate readiness for movement to the technologist. FIGS. 8A and 8B show how the coordination of mask 22 and detector 40 movement in translation step S134 is effected in a simple embodiment with two images. FIG. 8A shows detector 40 and mask 22 placed in position for the initial image. Once the first exposure is complete, both detector 40 and mask 22 then translate into position for the next image. Translation is triggered automatically, by detection of exposure, or is triggered by a command entry by the technologist. For this embodiment, it should be noted that x-ray tube 20 remains stationary; only exposure mask 22 moves for redirecting the x-ray beam toward the second DR detector position. FIG. 9 relates the movement of exposure mask from an initial position to two alternate positions for obtaining a long-length image, here using, as mask translation control 24, gravity and positioning pins 52 that are controlled by solenoids (not shown). As the progression in FIG. 9 shows, pins 52 are simply moved outwards in order to drop exposure mask 22 to the next position for imaging. The timing diagram at the top of FIG. 9 indicates the relative timing of exposure mask movement, relative to exposure. Once exposure completes, the next level of pins 52 are pulled outwards and exposure mask 22 then drops into the next position for capturing the subsequent image. It can be readily appreciated that while the use of gravity for translating collimator mask 22 between positions has advantages, any of a number of other mechanisms are usable for this purpose, including servo motors or other devices.

One aspect of the present invention relates to sensing that exposure has taken place and has terminated, so that translation step S134 (FIG. 3) can begin. At exposure mask 22, as shown in FIG. 9, sensor 28 responds to the beginning and ending of exposure and provides a signal that indicates termination of x-ray emission from the x-ray source so that translation can now take place. This signal is directed to mask translation control 24 (FIG. 1), enabling actuation of components that move exposure mask 22 to the next position. In FIG. 9, for example, the solenoids or other devices that move the next set of pins 52 are then actuated by mask translation control 24 once the proper signal from sensor 28 is received. Advantageously, obtaining this signal from sensor 28 does not depend on any type of direct communication with a host controller or with DR detector 40, simplifying the use of exposure mask 22 as a retrofit device. In one embodiment, sensor 28 is a photocell. The trailing edge or other transition of the photocell signal indicates termination of exposure for the current image. Springs or other mechanisms are alternately usable to position and support exposure mask 22.

Figure 10:
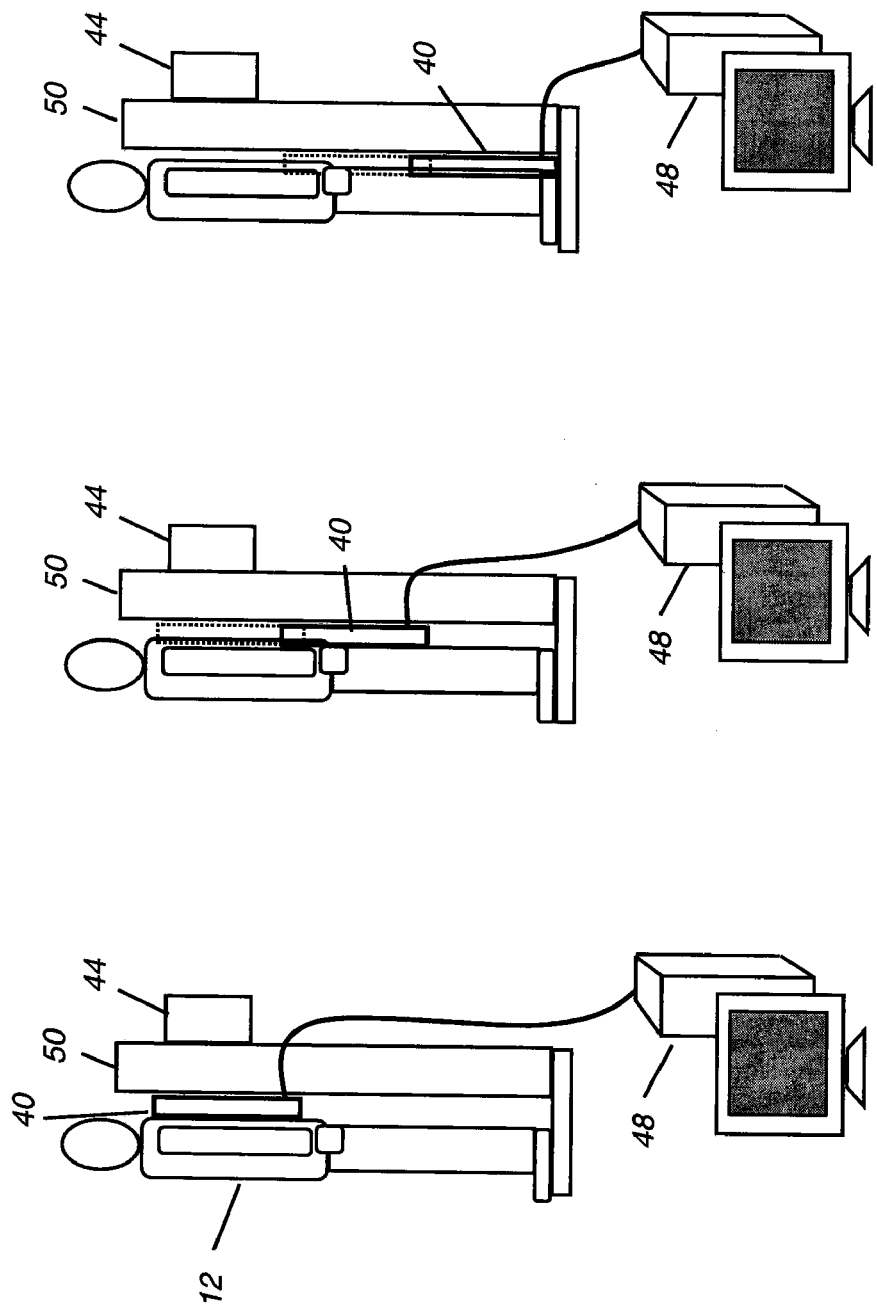
FIG. 10 is a diagram showing positioning of a DR detector along a transport column.

The schematic block diagram of FIG. 10 shows an embodiment in which DR detector 40, mounted on transport column 50, communicates with DR control processor 48 to provide a signal indicating that it has detected that exposure is complete and to initiate processing and transmission of the image data. In addition, this indicates to DR translation control 44 that translation of DR detector 40 to its next imaging position can begin. The communication link between DR detector 40 and control processor 48 is through a wired or wireless connection.

Figure 11:
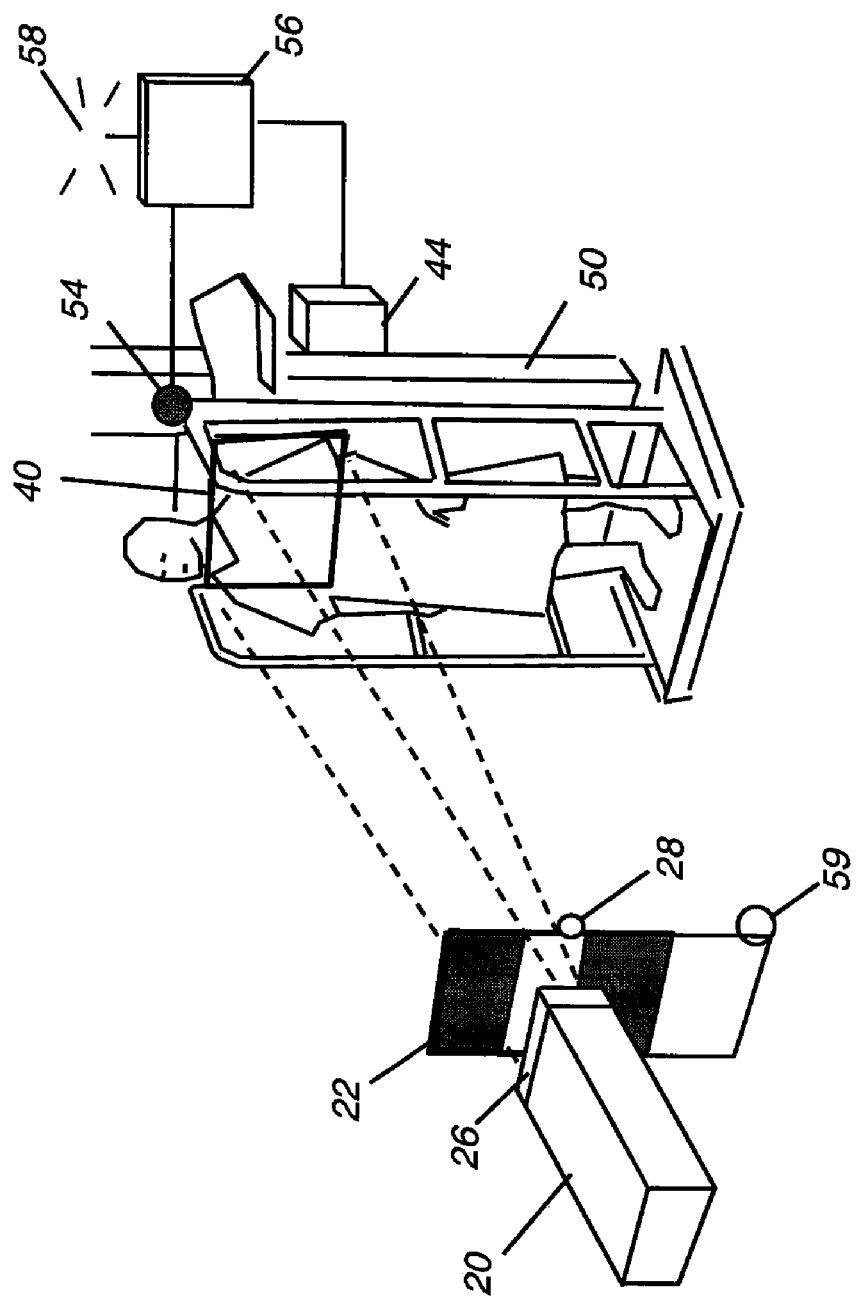
FIG. 11 is a perspective view showing an alternate embodiment with a sensor and indicator at the transport column.

In the alternate embodiment shown in FIG. 11, a separate sensor 54 is provided as part of transport column 50 or, optionally, as an attachment to DR detector 40 or some other component. Sensor 54 operates similarly to sensor 28, indicating that exposure is in process or has been completed, so that translation by DR translation control 44 can begin. Sensor 54 could be an audio sensor or photosensor, for example. A control logic processor 56 is in operative communication with sensor 54 in order to provide the properly timed signal to DR translation control 44 following exposure. In addition, an optional indicator 58 is also provided, with one or more functions. Indicator 58, or, alternately an audible annunciator, is energized when DR detector 40 is ready for exposure, following any downloading, refresh, translation, and other equipment-readying operation. This can be of assistance to the technologist, indicating that the next exposure can be initiated from operator console 32 (FIG. 1). This can be particularly advantageous, since it generally takes a few seconds for each of these readying operations to execute, and thus helps to reduce wasted time and reduce noise while the operator waits for a time interval before initiating the next exposure cycle. Actuation of another optional indicator 59 indicates when exposure mask 22 is ready and in position.

As is again clear from FIG. 11, asynchronous operation of the respective translation mechanisms for exposure mask 22 and DR detector 40 allows both devices to be moved at the proper time, without requiring any communication between them or communication by both of them to the same control logic device. An additional indicator (not shown) optionally indicates that exposure is taking place.

Figure 12:
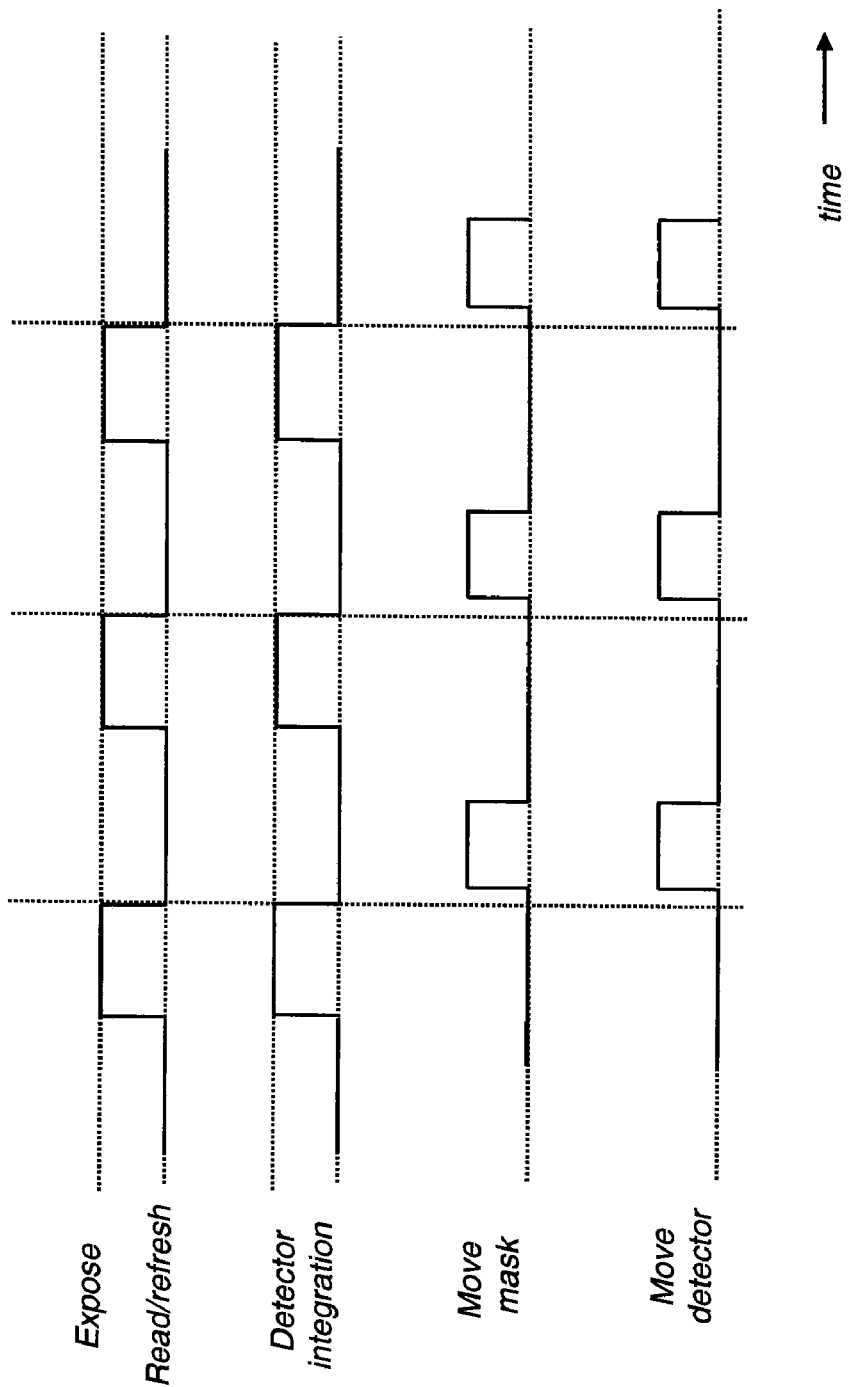
FIG. 12 is a timing diagram showing the timing of mask and detector movement relative to exposure and refresh timing.

The timing diagram of FIG. 12 shows a sequence for obtaining three separate images in a long-length imaging application using the apparatus and methods of an embodiment of the present invention. Detector integration is synchronous with exposure and is best terminated immediately when exposure has stopped. For example, referring to FIG. 11, a signal from sensor 54 is used to terminate detector 40 integration when the end of the exposure is reached in one embodiment. This arrangement is advantageous for DR systems where integration would otherwise be set for a fixed time, helping to reduce unwanted signal noise from being inadvertently received after exposure has been terminated. Following exposure termination, the respective translation subsystems for both DR detector 40 and exposure mask 22 are actuated, translating these devices to the next imaging position. In one embodiment, translation of DR detector 40 and mask 22 occurs while image processing, image data transfer, and refresh cycles are taking place, without additional impact on overall response or cycle time.

In another embodiment, one or both sensors 28 and 54 are not used and a timed interval is used for determining when exposure has been completed and translation of one or both components is allowed. However, this type of solution is generally less advantageous than using sensors, since a "worst-case" timing approximation would be required. Alternately, timing from the beginning of exposure sensed by one or both sensors 28 and 54 is usable as an estimate for indicating the termination of exposure so that translation of one or both components is needed. Thus, a signal is used to begin timing of a predetermined exposure interval in such an embodiment.

In yet another embodiment, one or both sensors 28 and 54 are audio sensors, triggered by the beginning and ending of an audible beep that is provided during exposure. In many environments, for example, an audible beep must be emitted by x-ray equipment during exposure time. Thus, detecting the termination of the audible beep serves as a useful trigger for indicating that exposure has terminated and that translation of one or both DR detector 40 and exposure mask 22 is appropriate.

As has been noted earlier, embodiments of the present invention can serve as a retrofit solution to provide long-length imaging to a conventional DR detection system. For this purpose, exposure mask 22 is attached or mounted against collimator 26 in any of a number of ways. In one embodiment, exposure mask 22 is magnetically coupled to collimator 26. Mask translation control 24 for exposure mask 22 may be battery powered (e.g., shown as battery in FIG. 1).

Because it is non-invasive and requires no fasteners, this embodiment is particularly advantageous as a retrofit to an existing x-ray system. Similarly, transport column 50 can be installed and used with an existing x-ray system, including systems designed for conventional film or CR imaging. Transport column 50 is also usable with a system that directs x-ray radiation over a smaller area, such as a system that rotates x-ray tube 20 or one that directly manipulates collimator 26 blades to reduce the beam path geometry to suit DR detector dimensions.

Referring back to the operation sequence shown in FIG. 3, methods for image stitching step S140 are known to those skilled in the diagnostic imaging arts. As was described with reference to FIGS. 4 and 5, an overlap area P is typically used along image segments in order to assist the stitching operation for forming the composite image.

It is noted that a kit can be provided for retrofitting/adapting an apparatus for capturing long length X-ray images of a subject as described above.

The invention has been described in detail with particular reference to a presently preferred embodiment, but it will be understood that variations and modifications can be effected within the spirit and scope of the invention. For example, any of a number of types of motors or other actuators could be used for translating the positions of the DR detector or exposure mask. Long-length imaging can be effected with the patient in the vertical or supine position, or other suitable position. Although the description and examples given in this disclosure show vertical imaging arrangements, the same principles also apply where long-length imaging is performed along a horizontal or diagonal path or some other path. Long-length imaging can also be done for inanimate objects, such as pipelines or other subjects that must be imaged and whose length or width exceeds the dimensions of the DR detector. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST

12. Patient
20. X-ray tube
22. Exposure mask
23. Focal spot
24. Mask translation control
26. Collimator
28. Sensor
30. Control circuitry
32. Operator console
40. DR detector
44. DR translation control
46. Display
48. DR control processor
50. Transport column
52. Pin
54. Sensor
56. Control logic processor
58, 59. Indicator
60. Imaging apparatus
80*a*, 80*b*. Image
90, 96. Stored settings
S100. Setup step
S110. X-ray exposure technique setup step
S120. Exposure and processing step S130. Decision step
S134. Translation step
S140. Image stitching step
S150. Image output step
S200. Initial setup step
S210. Storage step
S220. Looping step
S300. Initial setup step
S310. Storage step
S320. Looping step
$A_n$. Aperture
A, B. Positions
$E_n$, $E_n'$. Exposure field size
$H_n$. Tube stop position
$H_{top}$ Floor to top of radiation field;
$H_{bot}$ Floor to bottom of radiation field.
L. Exposure length
$L_d$, $L_d'$. Effective exposure length
P. Exposure overlap

What is claimed is:

1. An apparatus for obtaining a long-length x-ray image of a subject, comprising:
   an x-ray source;
   a first sensor configured to sense x-ray transmission from the x-ray source and to generate a first signal that indicates termination of x-ray emission from the x-ray source;
   a digital radiography detector that is energizable to generate image data after receiving x-ray emission from the x-ray source;
   a detector transport apparatus actuable in response to the first signal to translate the digital radiography detector from at least a first detector position to a second detector position for generating image data at each detector position;
   a processor in communication with the digital radiography detector for obtaining the image data of the subject that is generated from the detector;
   a movable mask operatively associated with the x-ray source and providing an aperture that directs x-rays from the x-ray source toward the subject for capturing a plurality of separate images of the subject on the digital radiography detector;
   a second sensor operatively associated with the movable mask to produce a second signal in response to detecting X-ray emission from the source; and
   a mask translation control responsive to the second signal for moving the movable mask from at least a first mask position to a second mask position for exposing an area of the subject.

2. The apparatus of claim 1 wherein the movable mask is coupled to a collimator of the x-ray source.

3. The apparatus of claim 1 wherein the movable mask is removably or permanently coupled to the x-ray source.

4. The apparatus of claim 1 wherein the detector transport apparatus comprises one or more of a spring, a servo motor, and a solenoid.

5. The apparatus of claim 1 wherein the mask translation control further comprises one or more of a spring, a servo motor, and a solenoid.

6. The apparatus of claim 1 wherein the mask translation control uses gravity for moving the mask.

7. The apparatus of claim 1 wherein the first sensor is an audio sensor or a photosensor.

8. The apparatus of claim 1 wherein the first sensor or the second sensor is an audio sensor or a photosensor.

9. The apparatus of claim 1 wherein the detector transport apparatus actuable in response to the first signal to translate the digital radiography detector and the mask translation control responsive to the second signal for moving the mask operate independently from each other.

10. The apparatus of claim 1 where a single controller does not control both the detector transport apparatus and the mask translation control.

11. The apparatus of claim 1 further comprising an indicator that is actuable to indicate that the digital radiography detector is ready for exposure.

12. The apparatus of claim 1 further comprising an indicator that is actuable to indicate that the digital radiography detector is ready for translation to the second detector position.

13. A method for obtaining a long-length x-ray image of a subject, comprising:
    positioning a digital radiography detector at a first detector position relative to the subject;
    positioning a movable mask to a first mask position relative to an x-ray source that directs exposure energy onto the digital radiography detector at the first detector position;
    energizing the x-ray source to expose the subject at the first detector position;
    obtaining a first signal from a first sensor that indicates termination of x-ray emission from the x-ray source;
    obtaining image data from the digital radiography detector at the first detector position;
    obtaining a second signal from a second sensor that indicates termination of x-ray emission from the x-ray source;
    asynchronously actuating a detector transport apparatus to translate the digital radiography detector from the first detector position to a second detector position for generating image data responsive to the first signal and a mask transport apparatus to translate the movable mask to a second mask position that directs exposure energy onto the digital radiography detector responsive to the second signal;
    energizing the x-ray source to expose the subject at the second detector position;
    obtaining a third signal from the first sensor that indicates termination of x-ray emission from the x-ray source;
    obtaining image data from the digital radiography detector at the second detector position; and
    combining the image data from at least the first and second detector positions to form the long-length x-ray image.

14. The method of claim 13 further comprising manually setting up at least the first and second detector positions and storing the first and second positions in a memory.

15. The method of claim 13 wherein actuating the detector transport apparatus comprises energizing a motor or a solenoid.

16. The method of claim 13 wherein actuating the mask transport apparatus comprises energizing a motor or a solenoid.

17. An apparatus for obtaining a long-length x-ray image of a subject, comprising:
    an x-ray source;
    a first sensor that generates a first signal that indicates x-ray emission from the x-ray source;
    a digital radiography detector that is energizable to generate image data after receiving x-ray emission from the x-ray source;

a detector transport apparatus actuable in accordance with the first signal to translate the digital radiography detector from at least a first detector position to a second detector position for generating image data at each detector position;

a processor in communication with the digital radiography detector for obtaining the image data of the subject generated from the detector;

a movable mask operatively associated with the x-ray source and providing an aperture that directs x-rays from the x-ray source toward the subject for capturing a plurality of separate images of the subject on the digital radiography detector;

a second sensor operatively associated with the movable mask for producing a second signal in response to termination of X-ray emission from the source; and a mask translation control responsive to the second signal for moving the mask from at least a first mask position to a second mask position for exposing an area of the subject.

18. The apparatus of claim 17 wherein the first or second sensor is an audio sensor or a photosensor.

19. The apparatus of claim 17 wherein the detector transport apparatus comprises one or more of a spring, a servo motor, and a solenoid.

* * * * *